(12) United States Patent
Massaro et al.

(10) Patent No.: US 7,240,539 B2
(45) Date of Patent: Jul. 10, 2007

(54) TEST METHOD

(75) Inventors: Michael Massaro, Monroe, CT (US); Douglas Ryan Eli, Trumbull, CT (US); Thomas Nikolaos Morikis, Southington, CT (US); Christine Elizabeth Kennedy, Trumbull, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 11/019,406

(22) Filed: Dec. 22, 2004

(65) Prior Publication Data
US 2006/0130564 A1    Jun. 22, 2006

(51) Int. Cl.
*G01N 37/00* (2006.01)
(52) U.S. Cl. .................................... 73/60.11
(58) Field of Classification Search ............. 73/60.11
See application file for complete search history.

(56) References Cited

U.S. PATENT DOCUMENTS 4,651,000 A * 3/1987 Kravetz et al. ............. 250/303

FOREIGN PATENT DOCUMENTS

JP          61-79136 A  *  4/1986   ................ 73/60.11

OTHER PUBLICATIONS

Borochov, et al., "Senescence and the Fluidity of Rose Petal Membranes," Plant Physiol. (1982) 69, 296-299.
Proceedings of the IVth International Congress on Surface Active Substances, Brussels, Sep. 7-12, 1964.

* cited by examiner

*Primary Examiner*—Daniel S. Larkin
(74) *Attorney, Agent, or Firm*—Alan A. Bornstein

(57) ABSTRACT

A test method is described for comparing the relative affinity of products for a target substance using a substrate ordinarily and visibly sensitive to the products. The test method is useful in one embodiment for comparing the ability of harsh cleansers to remove fatty acids from the skin with mild cleansers that do not remove fatty acids to the same extent using a visually compelling substrate, such as a fresh cut flower.

6 Claims, 3 Drawing Sheets

TEST METHOD

BACKGROUND OF THE INVENTION

1. Field of the Invention

The invention relates to a test method for estimating the affinity of a product for a target substance, more specifically by treating a substrate that is noticeably affected when contacted by the product with the target substance and assessing the affinity of the product for the target substance by observing any change in the substrate upon application of the product to the coated or otherwise treated substrate.

2. The Related Art

Various tests for comparison of attributes of products have been used. Such tests involve e.g. a comparison of the acidity or alkalinity of the product using litmus paper. Other tests involve comparison of selected physical and chemical properties of the products such, as speed of dissolution of tablets, degree of foaming of detergent compositions and similar visual methods. Surprisingly, it has been found that products may be effectively compared by comparing their affinity for a target substance coated onto or contacted with a sensitive substrate where the substrate will evidence a noticeable change upon contact with the product in the absence of the target substance.

Personal cleansing products are frequently marketed based on their degree of mildness to the skin of the user. Clinical data collected from measurements of skin dryness and erythema are often referred to when comparing different personal cleansing products. However, such comparisons are frequently not dramatic enough to catch the attention of the average person who is still interested in selecting a mild cleansing product for their cleansing needs. Surprisingly, it has been found that a substrate that is noticeably or measurably sensitive to such cleansing products, such as a fresh cut flower, may be advantageously used to convey differences in mildness of cleansing products when employed according the present invention.

SUMMARY OF THE INVENTION

In one aspect of the invention is a method for estimating the affinity of a product for a target substance (defined as the ability of the product to dissolve, emulsify, react or complex with the target substance including any combination of the foregoing), including but not limited to the steps of:

a. treating at least a portion of a substrate capable of changing its appearance after interacting with said product, with said target substance in an amount effective to form a barrier with the portion of the substrate;

b. contacting the treated portion of the substrate with said product under conditions effective to degrade the barrier properties of said target substance; and c. detecting a change in appearance of the substrate at the site of the degradation of the barrier.

In another aspect of the invention is a chemical test method for comparing the ability of soap and/or other harsh cleansing compositions to remove natural substances that protect human or animal skin with the ability of mild skin cleansing composition(s) to preserve the natural substances that protect skin during personal cleansing, including but not limited to the steps of:

a. coating a first and a second fresh cut flower with one or more C12-22 fatty acid(s) to form at least a partial barrier on the surface of the first and second flowers;

b. contacting the first coated flower with soap and/or other harsh cleansing solution under conditions effective to compromise the barrier properties of the fatty acid(s) deposited on the flower in step (a);

c. contacting the second coated flower with a mild cleansing solution using the same conditions as in step (b); and d. comparing the appearance of the first flower with the appearance of the second flower.

Preferred embodiments of the invention will now be described by way of example with reference to the accompanying photographs.

BRIEF DESCRIPTION OF THE PHOTOGRAPHS

DETAILED DESCRIPTION OF THE INVENTION

Figure 1:
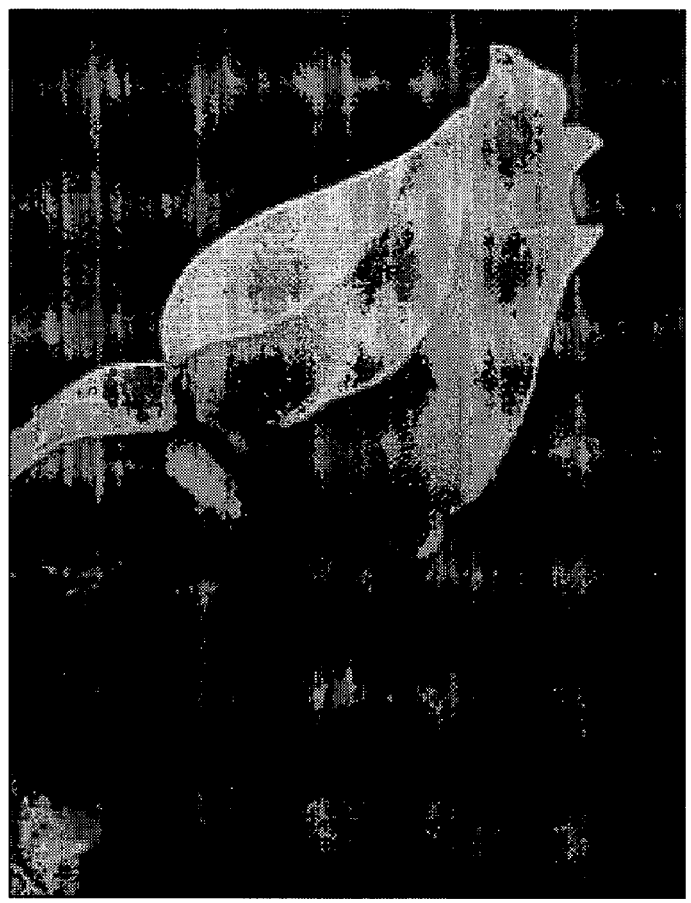
FIG. 1 is a photograph of a fresh cut rose (*Rosa* hybrid) just prior to coating with stearic acid.

In one aspect of the invention is a method for estimating the affinity of a product for a target substance including but not limited to the steps of:

a. treating at least a portion of a substrate capable of changing its appearance after interacting with said product (preferably where the interaction of the substrate with the product is noticeable within 24, 16, 8, 2 or 1 hour(s)), with said target substance in an amount effective to form a barrier with the portion of the substrate;

b. contacting the treated portion of the substrate with said product under conditions effective to degrade the barrier properties of said target substance; and c. detecting a change in appearance of the substrate at the site of the degradation of the barrier.

Preferably, the test method of claim 1 further includes comparing the affinity of a first product to the affinity of a second product for the target substance simultaneously or sequentially. More preferably, the deposition of the target substance on the substrate proceeds by a coating, reaction or complexation mechanism or a combination thereof. Advantageously, at least one of the products to be tested interacts with the target substance by at least partial solubilization, partial emulsification, chemical reaction, complexation or any combination thereof so as to degrade the barrier properties of the target substance.

In a preferred embodiment, the substrate is composed of a synthetic material, a natural material or a combination thereof. A natural material that is especially useful are flower petals from e.g. a fresh cut rose (*Rosa* species or hybrid). Advantageously, the product is selected from skin care and cleansing compositions containing at least about 1% by wt. of a surfactant. Preferably, the target substance is selected from one or more components that protect human or animal skin from moisture loss (such as fatty acids or other components of skin or any combination of the foregoing).

In another aspect of the invention is a chemical test method for comparing the ability of soap and/or other harsh cleansing compositions to remove natural substances that protect human or animal skin with the ability of mild skin cleansing composition(s) to preserve the natural substances that protect skin during personal cleansing, including but not limited to the steps of:

a. coating a first and a second fresh cut flower (preferably selected from a rose (*Rosa* species or hybrids) with one or more C12-22 fatty acid(s) to form at least a partial barrier on the surface of the first and second flowers;

b. contacting the first coated flower with soap and/or other harsh cleansing solution under conditions effective to compromise the barrier properties of the fatty acid(s) deposited on the flower in step (a);

c. contacting the second coated flower with a mild cleansing solution using the same conditions as in step (b); and d. comparing the appearance of the first flower with the appearance of the second flower.

Except in the operating and comparative examples, or where otherwise explicitly indicated, all numbers in this description indicating amounts of material ought to be understood as modified by the word "about".

The following example will more fully illustrate the embodiments of this invention. All parts, percentages and proportions referred to herein and in the appended claims are by weight unless otherwise illustrated. Physical test methods are described below:

EXAMPLE

Figure 2:
FIG. 2 is a photograph of a fresh cut rose (*Rosa* hybrid) coated with stearic acid and tested with a mild cleansing composition—toilet bar A—according to one embodiment of the present invention.
Figure 3:
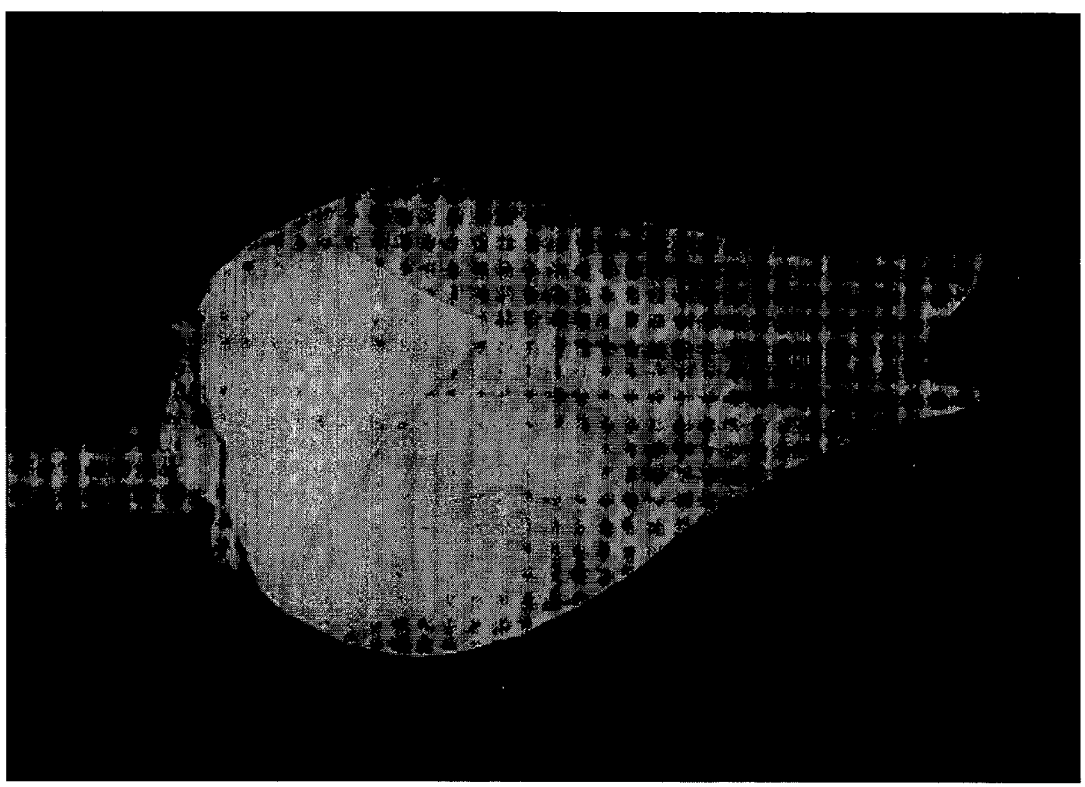
FIG. 3 is a photograph of a fresh cut rose (*Rosa* hybrid) coated with stearic acid and tested with a harsh cleansing composition—toilet bar U according to one embodiment of the present invention.

A number of commercially available toilet bars were tested as summarized in Table 1 using the inventive method as described below. It was seen that the products that are considered harsh to the skin according to clinical testing and/or other criteria caused a fresh cut rose to wilt noticeably as illustrated in FIG. 2 while products that are considered to be mild to the skin according to the above criteria did not noticeably affect the texture or appearance of the rose as illustrated in FIG. 3 using bar "A". A generic soap bar "U" was tested as a control as shown in FIG. 2 containing 85% by wt. of tallow/coco soap (82/18) that is made by treating fatty acids from oils and fats with caustic.

TABLE 1

| Toilet Bar Composition Comparison (from ingredient list on package) | | | | | | | | | | | | | | | | | | | | | |
|---|---|---|---|---|---|---|---|---|---|---|---|---|---|---|---|---|---|---|---|---|---|
| | A | B | C | D | E | F | G | H | I | J | K | L | M | N | O | P | Q | R | S | T | U |
| Synthetic Surfactants and/or Soaps | | | | | | | | | | | | | | | | | | | | | |
| Sodium Cocoyl Isethionate | x | | | | | | | | | | | | | | | | | | | | |
| Sodium Tallowate | x | x | x | x | x | x | x | | x | | x | x | x | x | x | x | x | x | x | x | x |
| Sodium Isethionate | x | | | | | | | | | | | | | | | | | | | | |
| Sodium Stearate | x | | | | | | | | | | | | | | | | | x | | | |
| Sodium Lactate | | | | | | | | | | | | | | | x | | | | | | |
| Sodium Cocoate | x | x | | x | x | x | x | | x | | x | | x | x | x | x | x | x | | | x |
| Sodium Palm Kernelate | x | x | | x | x | x | x | | | x | x | x | x | | x | | | x | x | | |
| Sodium Palmate | | x | | x | | x | | | x | | | x | | | | | x | | | | |
| TEA Cocoate | | | | | | | | | | | | | | | x | | | | | | |
| Magnesium Tallowate | | | | | | x | | x | | | | | | | | | | | | | |
| Magnesium Cocoate | | | | | | x | | | | | | | | | | | | | | | |
| Sodium cocoglyceryl ether sulfonate | | | | | | x | | | | | | | | | | | | | | | |
| Cocamidopropyl Betaine | x | | | | | | | | | | | | | | | | | | | | |
| Sodium Laureth Sulfate | | | | | | | | | | | | | | | x | | | | | | |
| Emollients, humectants, plant extracts and/or skin feel aids | | | | | | | | | | | | | | | | | | | | | |
| Stearic Acid | x | | | x | | | x | | | | x | | | | | x | | | | | |
| Coconut Acid | x | x | | x | x | x | x | | | | x | x | | | x | x | | | | x | |
| Palm Kernel Acid | | | | x | | x | | | | | x | | | | | | | | | | |
| Palm Acid | | x | | | x | | x | | | | x | | | | | | | | | | |
| Tallow Acid | | | | | x | x | x | | | | | | | | | x | | | | | |
| Prunis Dulcis | | | | | | | | | | | x | | | | | | | | | | |
| Butyrospermum parkii | | | | | | | | | | | x | | | | | | | | | | |
| Glycerin | | x | | x | x | | x | x | x | x | x | x | x | x | x | x | x | x | x | x | |
| Milk Protein | | | | | | | | | | | | x | | | | | | | | | |
| Lanolin | | | | | | | | | | | | x | | | | | | | | | |
| Sorbitol | | x | | | x | | x | | | | | | | x | x | | | | | | |
| Lanolin Alcohol | | | | | | | | | | | | | | | | | | x | | | |
| Paraffinum Liquidum | | | | | | | | | | | | | | x | | | | x | | | |
| Sodium PCA | | | | | | | | | | | | | | x | | | | | | | |
| Octyldodecanol | | | | | | | | | | | | | | x | | | | x | | | |
| Disteardimonium hectorite | | | | | | | | | | | | | | x | | | | x | | | |
| Lotus Extract | | | | | | | | | | | | | | x | | | | | | | |
| Elaeis Guineesis | | | | | | | | | | | | | | | x | | | | | | |
| Olea Euopaea | | | | | | | | | | | | | | | x | | | | | | |

TABLE 1-continued

Toilet Bar Composition Comparison (from ingredient list on package)

| | A | B | C | D | E | F | G | H | I | J | K | L | M | N | O | P | Q | R | S | T | U |
|---|---|---|---|---|---|---|---|---|---|---|---|---|---|---|---|---|---|---|---|---|---|
| Tetradibutyl Pentaerithrityl hydroxyhydrocinnamate | | | x | | | | | | | | | | x | x | | | | | | | |
| Acacia Farnesiana | | | | | | | | | | | | x | | | | | | | | | |
| Helianthius Annuus | | | | | | | | | | | | x | | | | | | | | | |
| Lemon Peel Extract | | | | | | | | | | | | | x | | | | | | | | |
| Decyl Glucoside | | | | | | | | | | | | | x | | | | | | | | |
| Prunis Dulcis | | | | | | | | | | | | | | x | | | | | | | |
| Aloe Barbadensis Leaf Juice | | | x | | | | | | | | | | | | | | | | | | |
| PEG 12 | | | x | | | | | | | | | | | | | | | | | | |
| Cocoa Seed Butter | | | x | | | | | | | | | | | | | | | | | | |
| Dipropylene Glycol | | | | | | | | | | | | | | | | x | | x | | | |
| Propylene Glycol | | | x | | | | | | | | | x | | | | | | | | | |
| Sodium Lactate | | | | | | | | | | | | x | | | | | | | | | |
| Citrus Limonum | | | | | | | | | | | | x | | | | | | | | | |
| Potassium Ricinoleate | | | | | | | | | | | | | | x | | | | | | | |
| Ricinoleic acid | | | | | | | | | | | | | | x | | | | | | | |
| PEG 75 Lanolin | | | | | | | | | | | | | | x | | | | | | | |
| Sucrose | | | | | | | | | | | | | | x | | | | | | | |
| PEG 6 Methyl Ether | | x | | | | | | | | | | | | | | | | | | | |
| Fragrance | x | x | | x | x | x | x | x | x | x | x | x | x | x | x | x | | | x | x | |
| Preservatives, fillers, salts and/or pH adjusters | x | x | | x | x | x | x | x | x | x | x | x | x | x | x | x | x | x | x | x | x |

Notes:
Product name, manufacturer, location.
A: Dove ® Unilever (Greenwich, CT)
B: Dial ® Dial Corporation (Scottsdale, Arizona)
C: Ivory ® Proctor and Gamble (Cincinnati, OH)
D: Irish Spring ® Colgate (New York, NY)
E: Tone ® Dial Corporation Scottsdale, Arizona)
F: Zest ® Proctor and Gamble (Cincinnati, OH)
G: Coast ® Dial Corporation (Scottsdale, Arizona)
H: Zest ® Proctor and Gamble (Cincinnati, OH)
I: Nuetro Roberts ® L. Manetti - Roberts & C.p.A.(Italy)
J: Le Petit Marsellais ® Laboratories Venome (France)
K: Monsavon ® Sare Lee (France)
L: Duru ® Evyap (Russia)
M: Palmolive naturals Original Colgate Palmolive (UK)
N: Palmolive Naturals Energizing ® Colgate Palmolive (UK)
O: Fa Refreshing ® Schwarzkopf & Henkel (Germany)
P: Nivea Bath Care ® Beiersdorf (Germany)
Q: La Toja ® Schwarzkopf & Henkel (Spain)
R: Magno ® Schwarzkopf & Henkel (Spain)
S: Heno de Pravia ® Gal (Spain)
T: Pearl (pink) ® PZ Cussons (UK)
U: Control 82/18 Soap Test Method:

The outer petals of a fresh cut rose (*rosa* hybrid) were removed so as to obtain an even teardrop shape (as illustrated in FIG. 1) and the rose was then coated in stearic acid, which is a natural moisturizer found in the skin. The coating is done by dipping the rose into molten stearic acid at 63° C. for one minute. After removing the rose from the stearic acid, the rose is immediately turned flower tip up to allow the stearic acid to flow down into the rose assuring a good coating of any gaps and tiny spaces. The coating should be smooth with no "crackling" appearance. Allow roses to cool and dry for at least 5 minutes at approx. 25 C.

Once the rose is coated, separate 10% solutions of cleansing compositions are prepared and placed in a water bath at 43° C. These solutions may be clear or have a milky or pearlized appearance. The solutions are stirred continuously. The roses are then suspended upside down, about half way up the bud, into the warm solutions. The roses are kept in solution at 43° C. for 55 minutes and then removed. Excess solution is rinsed off the rose under warm running water (1.2 L/min approximate flow rate). At the end of the test, the mild cleanser treated rose coating will be smooth and the rose itself will be undamaged as illustrated in FIG. 2 (although there may be some slight discoloration due to exposure to the warmth of the solution). The coating on the harsh soap-treated rose will have partially dissolved, and the rose will look brown and have a rough texture as shown in FIG. 3. The loss of integrity of the stearic acid coating allows the penetration of the soap solution into the body of the rose, turning it brown and indicating, by analogy, the potential for skin damage.

The example is a demonstration of how soap damages and dissolves one of the critical components of the skin's protective layer (e.g. stearic acid), significantly more than a product having substantially more mild synthetic surfactants than soap. Stearic acid is one of the natural lipids found in the stratum corneum lipid layer, which makes up the protective moisture barrier of skin. The rose serves as both the substrate which holds the protective layer of stearic acid, and a model of the living tissue which it protects. Although not wishing be bound by the following theoretical mechanism, it is believed that the harshness and high pH of high levels of soap combine to dissolve the stearic acid coating deposited on the rose allowing the surfactant solution to penetrate and distort the flower petals. A similar dissolution of stearic acid (as well as other fatty acids in the barrier) will occur in skin when exposed to soap. When exposed to a mild cleansing solution however, which has a milder, pH neutral surfactant and optionally an emollient such as free fatty acids (e.g. stearic acid), the integrity of the stearic acid coating is maintained, both on the rose or in the skin.

A variety of light colored roses (ivory, peach, pink, yellow) have been employed. The test is effective notwithstanding flower color but it is easier to see the results with the lighter colors. Preferably, substrates that are considered fragile to the average user of cleansing compositions are employed to dramatically convey the results. Roses and similar delicate fresh flowers are widely considered delicate and fragile with many qualities that are coveted in skin, such as a soft and smooth velvety texture.

Any convenient concentration of cleansing solution may be used for the test, up to the solubility limit and/or gel formation thereof. At concentrations lower than 10% by wt. the results are essentially the same, but a longer time to reach the end point of the test is observed. At higher concentrations, soap slurries tend to form gels that may interfere with the test.

The soap bars tested in Table 1 fall into four types of bars that are widely marketed: a) plain soap bars that contain only soap, characterized by high pH (>10) and harshness to skin, b) superfatted soaps that contain small amounts of free fatty acids (2-6%) that improve bar properties and have a small positive effect on mildness. The pH of these soaps is typically in the range (9-10) and these are also considered harsh to skin. c) Transparent soaps that contain modest levels of glycerin, characterized by high pH (>10) and harshness to skin; and d) combination soaps that contain small amounts of mild synthetic surfactants in addition to the soap. This combination helps improve the mildness of these bars and are typically are in a pH range 8-9, but are still significantly harsher to skin compared to the most mild cleanser bars.

The inventive test also serves to emphasize the irritancy caused by plain soaps that often leads to the skin feeling taut and dry. This tight dry feeling is the result of damage to the stratum corneum, the outer protective layer of the skin that is responsible for regulating the water content of the epidermal layers. The stratum corneum is made up of corneocytes, dead cells derived from the differentiation and maturation of keratinocytes, held in a lipid matrix. Soaps damage this layer by interacting strongly with the corneocytes and the lipid matrix in the stratum corneum. Damage to this layer is characterized by a swelling of the outer layer of corneocytes, removal/disruption of the lipid matrix and increased water loss from this disrupted surface, associated with a lower skin hydration level. After repeated damage to the stratum corneum, these effects are manifested in visual and tactile changes to the properties of the skin; dry uplifted cells which appear as white flakes, visible white cracks or scaling in the skin surface, reddening of the affected region, rough texture and a feeling of tightness. Mild cleansing compositions do not damage the stratum corneum as soaps do. Mild cleansers interact minimally with the corneocytes and lipid matrix of the stratum corneum, do not disturb the skin's natural balance as much as soap and do not result in any significant increase of the water loss from the skin under conditions where soap causes an increase, and hence does not lead to a tight sensation and dry skin appearance as much as soap does.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A chemical test method for estimating the affinity of a product for a target substance, comprising the steps of:
    a. treating at least a portion of a substrate capable of changing its appearance after interacting with said product, with said target substance in an amount effective to form a barrier with the portion of the substrate wherein the target substance is selected from one or more components that protect human or animal skin from moisture loss;
    b. contacting the treated portion of the substrate with said product under conditions effective to degrade the barrier properties of said target substance;
    c. creating an image of a change in appearance of the substrate at the site of the degradation of the barrier; and
    d. comparing the image recorded in step c, with an image of at least a portion of a substrate treated with a second product that does not substantially degrade the barrier properties of said target substance.

2. The test method of claim 1 wherein the deposition tile target substance on the substrate proceeds by a coating, reaction or complexation mechanism or a combination thereof.

3. The test method of claim 1 wherein the product interacts with the target substance by at least partial solubilization, partial emulsification, chemical reaction, complexation or any combination thereof so as to degrade the barrier properties of the target substance.

4. The test method of claim 1 wherein the substrate is composed of a synthetic material, a natural material or a combination thereof.

5. The test method of claim 1 wherein the product is selected from skin care and cleansing compositions containing at least 1% by wt. of a surfactant.

6. A chemical test method for comparing the ability of soap and/or other harsh cleansing compositions to remove natural substances that protect human or animal skin with the ability of mild skin cleansing composition(s) to preserve the natural substances that protect skin during personal cleansing, comprising the steps of:
    a. coating a first and a second fresh cut flower with one or more C12-22 fatty acid(s) to form at least a partial barrier on the surface of the first and second flowers;
    b. contacting the first coated flower with soap and/or other harsh cleansing solution under conditions effective to compromise the barrier properties of the fatty acid(s) deposited on the flower in step (a);
    c. contacting the second coated flower with a mild cleansing solution using the same conditions as in step (b); and
    d. comparing the appearance of the first flower with the appearance of the second flower.

* * * * *